United States Patent
Johs (10) Patent No.: US 7,483,148 B1
(45) Date of Patent: Jan. 27, 2009

(54) ELLIPSOMETRIC INVESTIGATION OF VERY THIN FILMS

(75) Inventor: Blaine D. Johs, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 88 days.

(21) Appl. No.: 11/724,849

(22) Filed: Mar. 16, 2007

Related U.S. Application Data (63) Continuation-in-part of application No. 10/765,732, filed on Jan. 27, 2004, now Pat. No. 7,193,709.

(60) Provisional application No. 60/444,333, filed on Jan. 31, 2003.

(51) Int. Cl.
*G01B 11/02* (2006.01)
*G01J 4/00* (2006.01)

(52) U.S. Cl. .................. 356/504; 356/369

(58) Field of Classification Search .......... 356/450, 356/497, 498, 503, 504, 369
See application file for complete search history.

(56) References Cited

U.S. PATENT DOCUMENTS

| | | | |
|---|---|---|---|
| 4,105,338 A | 8/1978 | Kuroha | 356/118 |
| 4,826,321 A | 5/1989 | Coates et al. | 356/351 |
| 4,899,055 A | 2/1990 | Adams | 250/372 |
| 5,181,080 A | 1/1993 | Fanton et al. | 356/369 |
| 5,484,701 A | 1/1996 | Norton et al. | 250/372 |
| 5,517,312 A | 5/1996 | Finarov | 356/386 |
| 5,595,916 A | 1/1997 | Fujimura et al. | 437/8 |
| 5,793,480 A | 8/1998 | Lacey et al. | 356/73 |
| 5,798,837 A | 8/1998 | Aspnes et al. | 356/369 |
| 5,871,805 A | 2/1999 | Lemelson | 427/8 |
| 5,900,633 A | 5/1999 | Solomon et al. | |
| 5,900,939 A | 5/1999 | Aspnes et al. | 356/369 |
| 5,910,842 A | 6/1999 | Piwonka-Corle et al. | 356/369 |
| 6,278,519 B1 | 8/2001 | Rosencwaig et al. | 356/369 |
| 6,278,809 B1 | 8/2001 | Johnson et al. | 385/17 |
| 6,349,594 B1 | 2/2002 | Yabe | 73/150 |
| 6,573,999 B1 | 6/2003 | Yang | 356/632 |
| 6,605,482 B2 | 8/2003 | Celii et al. | 438/16 |
| 6,605,512 B2 | 8/2003 | Kiyota | |
| 6,741,353 B1 * | 5/2004 | Johs | 356/445 |
| 6,954,275 B2 * | 10/2005 | Choi et al. | 356/614 |
| 7,268,876 B1 * | 9/2007 | Johs | 356/369 |
| 7,345,765 B2 * | 3/2008 | Atanasov | 356/432 |
| 2002/0176081 A1 | 11/2002 | Opsal et al. | |

OTHER PUBLICATIONS

Data Analysis for Spectroscopic Ellipsometry, Thin Solid Films 234 (1993) by Jellison Jr.
Techniques for Ellipsometric Measurement of Thickness and Optical Constants of Thin Films McGahan et al. Thin Solid Films 234 (1993).

* cited by examiner

*Primary Examiner*—Michael A Lyons
(74) *Attorney, Agent, or Firm*—James D. Welch (57) ABSTRACT

Use of spectroscopic data obtained by investigation of a witness sample having a relatively thick dielectric on a surface thereof during deposition of a thin film onto the witness sample and onto a process sample having no, or a relatively thin dielectric on its surface, in characterizing thin film deposited onto the process sample.

6 Claims, 13 Drawing Sheets

ELLIPSOMETRIC INVESTIGATION OF VERY THIN FILMS

This application is a CIP of Ser. No. 10/765,732 Filed Jan. 27, 2004, (U.S. Pat. No. 7,193,709), and therevia Claims benefit of Provisional 60/444,333, Filed Jan. 31, 2003.

TECHNICAL AREA

The disclosed invention relates to the use of electromagnetic radiation to investigate thin films, and more particularly to a system and method of characterizing thin films on process samples by monitoring similar thin films on witness samples having relatively thick dielectric on a surface thereof.

BACKGROUND

While not limiting, as a relevant non-limiting example to which the present invention can be beneficially applied, it is disclosed that fabrication of MOSFET Transistors requires formation of a Gate Structure on a Semiconductor Substrate. Typical practice is to use Silicon as the Semiconductor Substrate, grow thermal $SiO_2$ on its surface, (which is a dielectric material), and then apply metal atop thereof to form said Gate Structure. When Gate $SiO_2$ thickness is below about 100 Angstroms, however, it becomes leaky and is subject to breakdown at too low of voltages applied to the metal. Investigation of deposited materials, other than $SiO_2$ onto the Semiconductor for use as the dielectric material in Gate Structures, is therefore being pursued. However, control of the properties of the dielectric material formed during a fabrication procedure are sensitive to changes in the procedure, which changes are often difficult to detect and control. The present invention recognizes this fact and the fact that the first step in developing repeatability in fabrication is developing the ability to accurately monitor thin films. Methodology which enables accurate monitoring of materials allows identification of deviations from optimum which can be correlated to what are often subtle changes in fabrication procedure parameters, which subtle fabrication procedure changes are not readily obvious unless it is known to specifically look for their presence as a result of detected deviations from intended fabrication end-results.

Further, as alluded to above, application of a thin metal film atop Gate Oxide or other dielectric material is necessary during MOSFET fabrication. In that light it is disclosed that even ellipsometric investigation of very thin films of any composition when deposited atop a thin dielectric film, (eg. 30-100 Angstroms), often does not result in data which can be used to accurately determine the thickness of said film.

Another area wherein very thin films require characterization, and to which the present invention is applicable, is that of tribiological coatings on hard drive heads.

The methodology of the invention disclosed herein can be applied to characterize and/or control formation of a thin film on a process system based upon investigation of the same film which is deposited onto a witness sample that has a relatively thick dielectric layer.

An article titled "Data Analysis for Spectroscopic Ellipsometry", Thin Solid Films, 234 (1993) is disclosed as it defines parameters $N=\text{Cos}(2\psi)$; $C=\text{Sin}(2\psi)\text{Cos}(\Delta)$, and $S=\text{Sin}(2\psi)\text{Sin}(\Delta)$ which are applied in the preferred embodiment of the disclosed invention.

A search of patents which focus the use of electromagnetic radiation to monitor thin films or the fabrication of thin films, has provided the following:

U.S. Pat. No. 6,573,999 to Yang;
U.S. Pat. No. 6,349,594 to Yabe;
U.S. Pat. No. 5,486,701 to Norton et al.;
U.S. Pat. No. 5,798,837 to Aspnes et al.;
U.S. Pat. No. 4,105,338 to Kuroha;
U.S. Pat. No. 5,181,080 to Fanton et al.;
U.S. Pat. No. 4,826,321 to Coates et al.;
U.S. Pat. No. 5,910,842 to Piwonka-Corle et al.;
U.S. Pat. No. 5,517,312 to Finarov;
U.S. Pat. No. 6,605,512 to Kiyota;
U.S. Pat. No. 5,900,633 to Solomon et al.;
U.S. Pat. No. 6,278,519 to Rosenscwaig et al.;
U.S. Pat. No. 4,899,055 to Adams;
U.S. Pat. No. 5,798,837 to Aspnes et al.;
U.S. Pat. No. 5,793,480 to Lacey et al.;
U.S. Pat. No. 5,900,939 to Aspnes et al.;
U.S. Pat. No. 5,595,916 to Fujimura et al.;
U.S. Pat. No. 6,605,482 to Celii et al.; and
Patent Application No. US 2002/0176081 A1.

Patents which discuss monitoring witness samples are:
U.S. Pat. No. 6,278,809 to Johnson et al.;
U.S. Pat. No. 5,871,805 to Lemelson;

Even in view of the identified prior art, need remains for methodology which enables evaluating and/or controlling formation of very thin films.

DISCLOSURE OF THE INVENTION

In a very general sense, the disclosed invention comprises a method for evaluating, and/or performing real time control of, the formation of very thin films utilizing spectroscopic electromagnetic radiation which is caused to interact therewith. The method can be applied to the case where there is one thin film present directly on a substrate surface, or where there are a sequence of adjacent thin films present on a substrate.

For insight, it is noted that thin film characterizing spectroscopic data can be obtained by causing a beam of electromagnetic radiation which comprises a multiplicity of wavelengths, to interact with, via reflection from or transmission through said thin film, and then enter a detector which provides intensity data vs. wavelength as output. Where ellipsometry is applied the data is obtained by causing a beam of electromagnetic radiation, which comprises a multiplicity of wavelengths to, after having a polarization state imposed hereupon by a polarizer, interact via reflection from or transmission through said thin film, pass through an analyzer and then enter a detector which provides intensity data vs. wavelength as output. Optionally, a compensator can be present in the beam pathway between the polarizer and analyzer, or a modulation element can be present in the path of the beam. Where ellipsometric data is obtained the present invention methodology can be practiced using any type of Ellipsometer, including those which provide that a Polarizer and/or Analyzer and/or Compensator rotate during data acquisition, and those which provide that the beam be modulated.

Continuing, as identified in the Background Section, where investigated films are very thin, (eg. less than 100 Angstroms), it becomes difficult to identify content in spectroscopic data which is definitely correlated to thin film characterizing parameters, such as dielectric constant and/or thickness.

Note that the just recited example can be beneficially applied to the case where a MOSFET Gate metalization is being deposited to a substrate on which is present less than 100 Angstroms of Gate Oxide or other Gate insulator material. The Witness Sample, having a much thicker, (eg. 500-5000 Angstroms or more), layer of similar Oxide or other Insulator, enables acquisition of a spectra which makes the detection of the thickness of the deposited metal much more pronounced. The effect is demonstrated graphically in the Detailed Description Section of this Specification, using Amorphous Silicon and Amorphous Carbon thin films on thick transparent dielectric.

The present invention comprises a method of monitoring fabrication of, or the end result of fabrication of a process sample comprised of a sequence of at least one very thin layer of material deposited thereonto, said layer having a thicknesses on the order of less than about 100 Angstroms, said method comprising the steps of:

a) providing a process sample and a witness sample, said process sample having relatively no, or a very thin layer of a dielectric on a surface thereof, and said witness sample having a relatively thick dielectric on a surface thereof;

b) before and/or during and/or after causing deposition of a thin layer of material on to both the prosess and witness samples, obtaining spectroscopic data from the witness sample by causing polychromatic electromagnetic radiation to interact with said witness sample and then enter a detector, to the end that said detector develops an output data for said witness sample;

c) analyzing said data to arrive at the thickness and/or optical constants of the material deposited onto the witness sample and attributing said result to the process sample.

(It is noted that where the optical constants of a deposited material are known and can be fixed, then the thickness of the deposited layer can be determined independently).

Said method can further comprise performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

Said method can use spectroscopic data derived from ellipsometric PSI and/or DELTA vs. wavelength for said witness sample, and can comprise at least one selection from the group consisting of:

$N = \cos(2\psi)$;
$C = \sin(2\psi)\cos(\Delta)$;
$S = \sin(2\psi)\sin(\Delta)$.

In particular, a difference in the spectroscopic data can be at least one selection from the group consisting of:

$(N_f - N_o)$;
$(C_f - C_o)$; and
$(S_f - S_o)$.

A preferred, but not limiting, approach provides that the spectroscopic data comprise a difference in an RMS value calculated from:

$$\sqrt{\frac{(N_f - N_0)^2 + (C_f - C_0)^2 + (S_f - S_0)}{3}}$$

where:
$N_o = \cos(2\psi)$;
$C_o = \sin(2\psi)\cos(\Delta)$;
$S_o = \sin(2\psi)\sin(\Delta)$;

correspond to said witness sample before, or at some intermediate time during a deposition of a thin film thereupon where a fabrication is being monitored; and $N_f = \cos(2\psi)$;
$C_f = \sin(2\psi)\cos(\Delta)$;
$S_f = \sin(2\psi)\sin(\Delta)$;

corresponds to said witness sample after deposition of said thin film thereupon, or perhaps at some later intermediate time after a deposition started, where a fabrication is being monitored.

While not limiting, the witness sample can be comprised of any dielectric, such as at least one selection from the group consisting of:

SiO2-Si;
$SiO_2$;
SiON;
HfO;
HfO—$SiO_2$.

It is noted that to emphasise the identified effect of the thin dielectric, the thin film should have very different optical constants therefrom.

The electromagnetic radiation used can comprise wavelengths in at least one selection from the group consisting of:

FIR;
IR;
NIR-VIS-NUV;
UV;
DUV; and
VUV;

where the relatively thick dielectric is selected to be optically transparent material at a selected wavelength range.

The disclosed invention will be better understood by a reading of the Detailed Description with reference to the Drawings.

SUMMARY OF THE INVENTION

It is therefore a purpose and/or objective of the disclosed invention to teach a method of investigating a process sample comprised of a sequence of at least one layer of material having a thicknesses on the order of less than about 100 Angstroms, by investigating a witness sample having a relatively thick dielectric present on a surface thereof onto which said at least one layer of material is also deposited.

It is another purpose and/or objective of the disclosed invention to teach a method of controlling depositon of a very thin film onto a process sample by using information determined by investigating a witness sample having a relatively thick dielectric on a surface thereof onto which said very thin film is also deposited.

It is yet another purpose and/or objective of the disclosed invention to teach that beneficial results can often be achieved by working with parameters derived from PSI ($\psi$) and DELTA ($\Delta$), which are known in the literature as N, C and S, said parameters being:

N=Cos(2$\psi$);
C=Sin(2$\psi$)Cos($\Delta$);
S=Sin(2$\psi$)Sin($\Delta$); and that a preferred approach utilizes said N, C, and S parameters at two times, (eg. before and after fabrication or at any two times during a fabrication procedure), expressed as a difference RMS value.

It is another purpose and/or objective yet of the disclosed invention to teach characterization of very thin absorbing films on witness samples which have a relatively thick layer of optically transparent material.

Other purposes and/or objectives of the disclosed invention will be apparent from a reading of the Specification and Claims.

DETAILED DESCRIPTION

Figure 1:
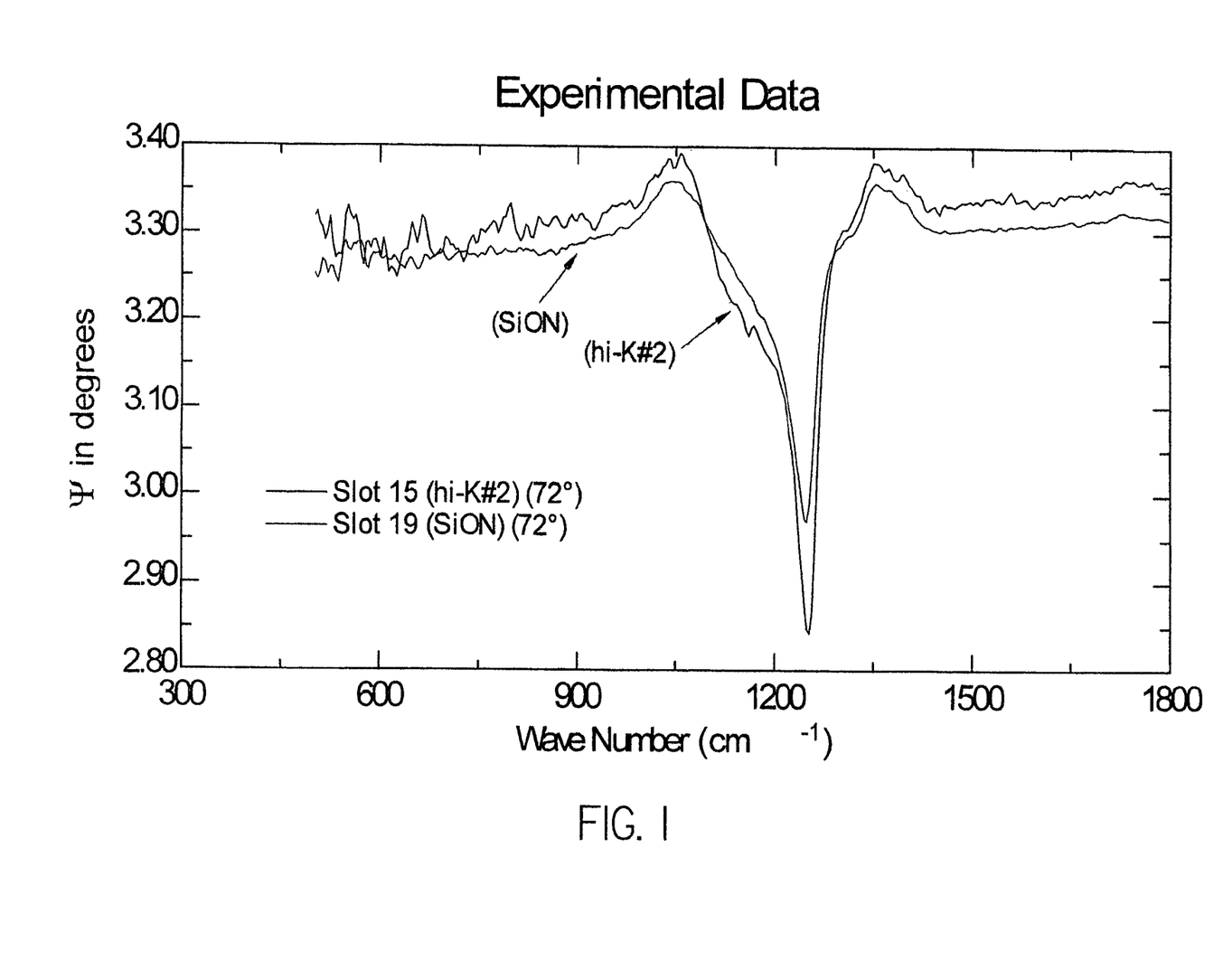
FIGS. 1 and 2 demonstrate, on the same plot, typical ellipsometric PSI ($\psi$) and DELTA ($\Delta$) Spectra obtained for two samples.
Figure 2:
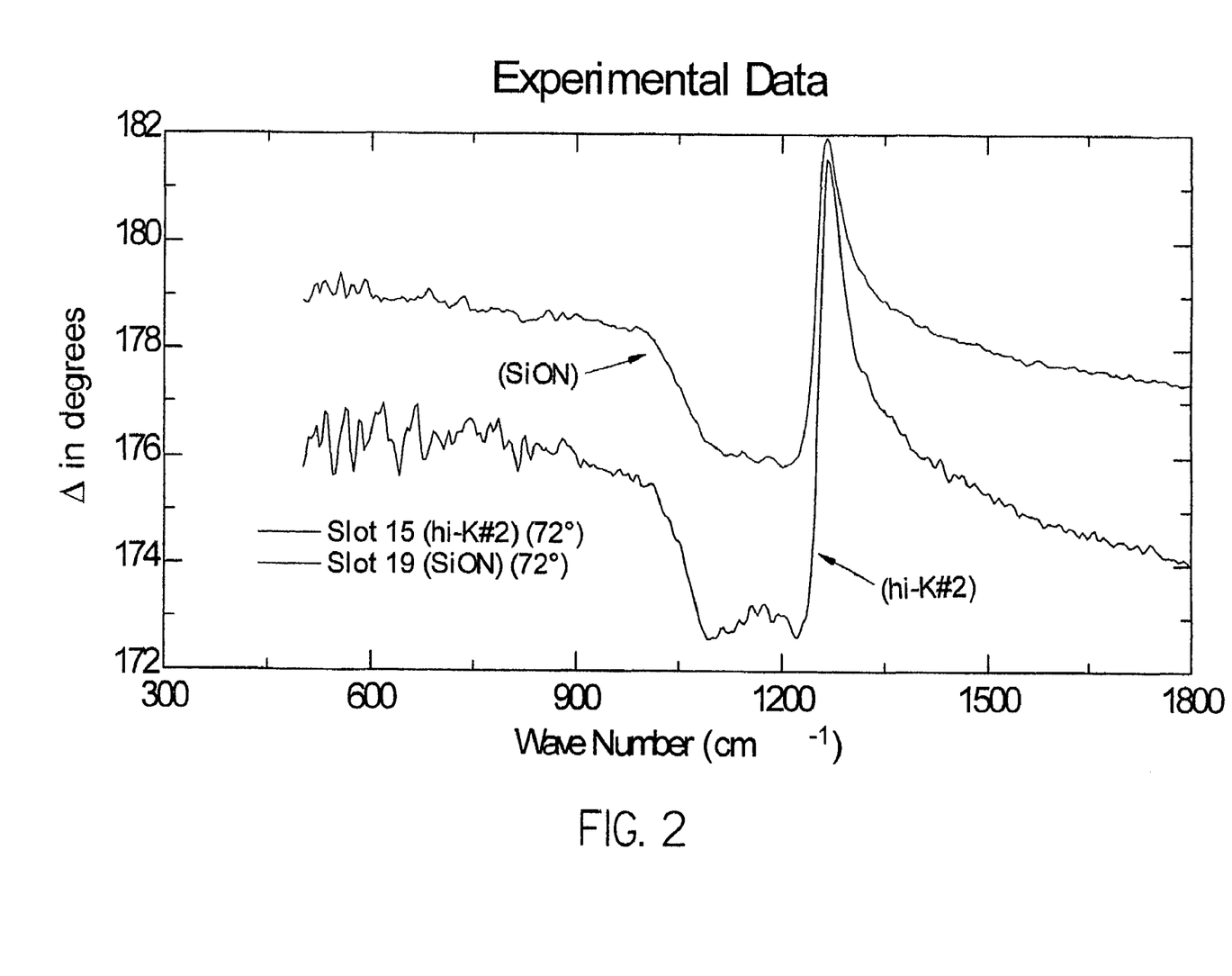
Figure 3:
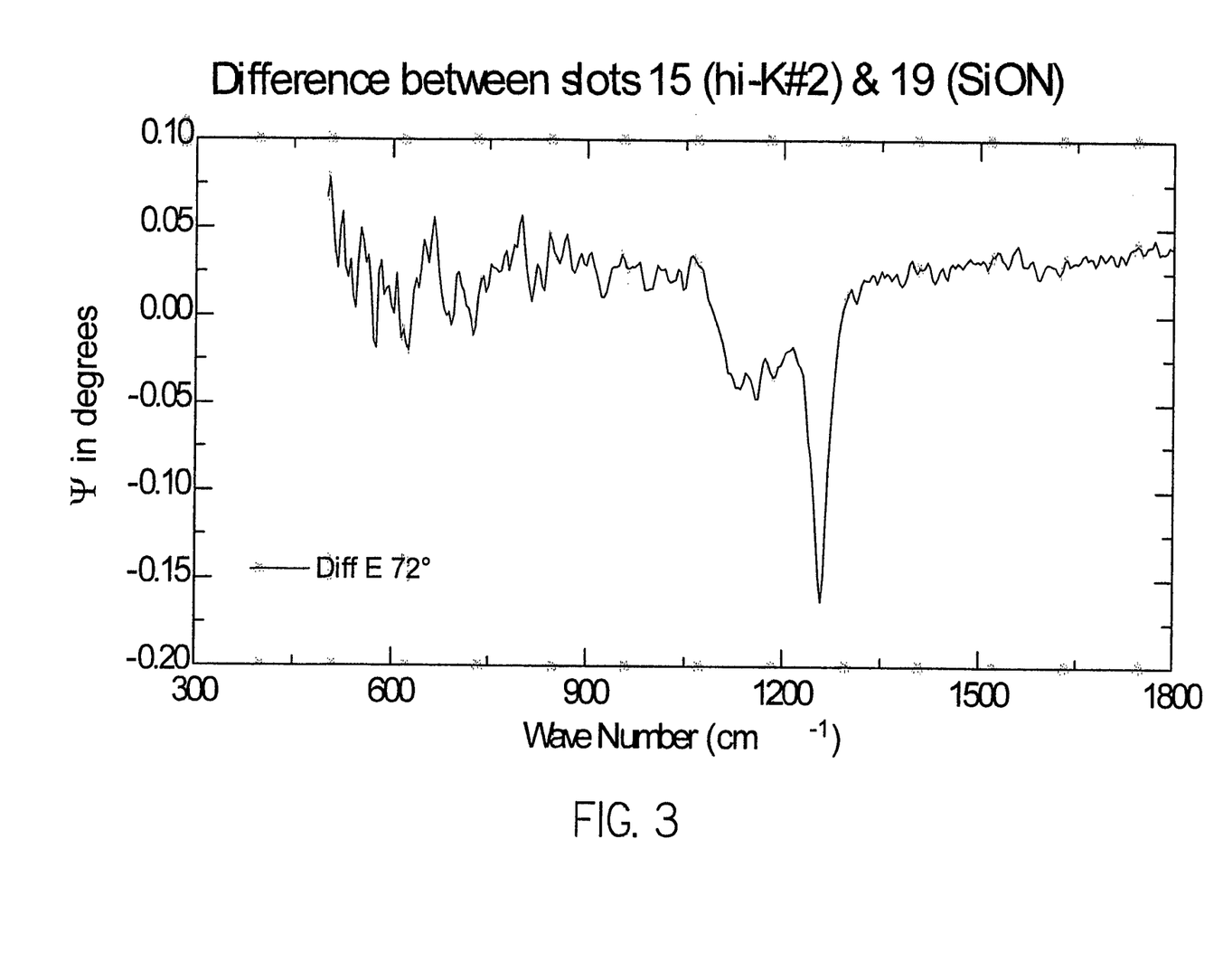
FIGS. 3 and 4 show differences in the PSI ($\psi$) and DELTA ($\Delta$) Spectra of FIGS. 1 and 2, respectively.
Figure 4:
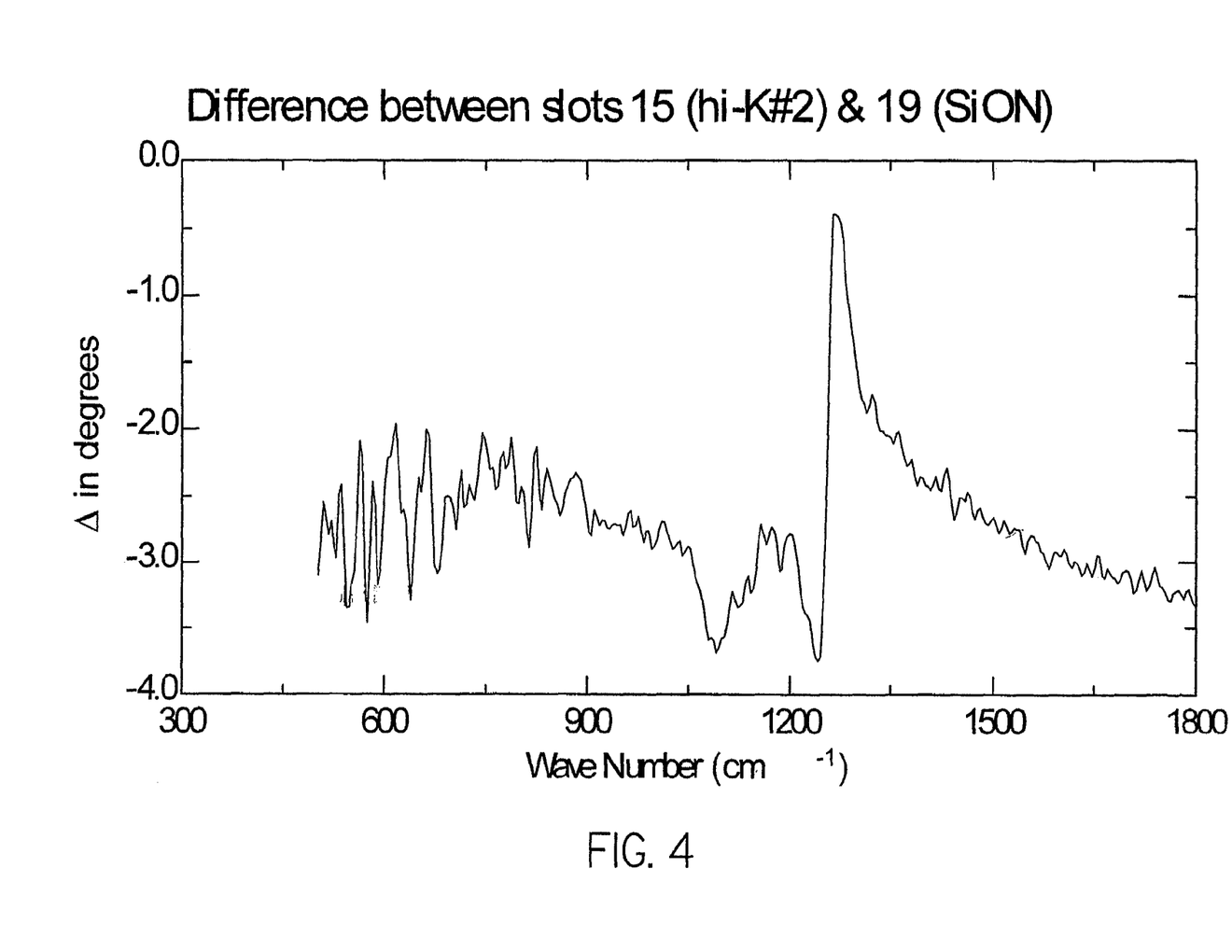
Figure 5:
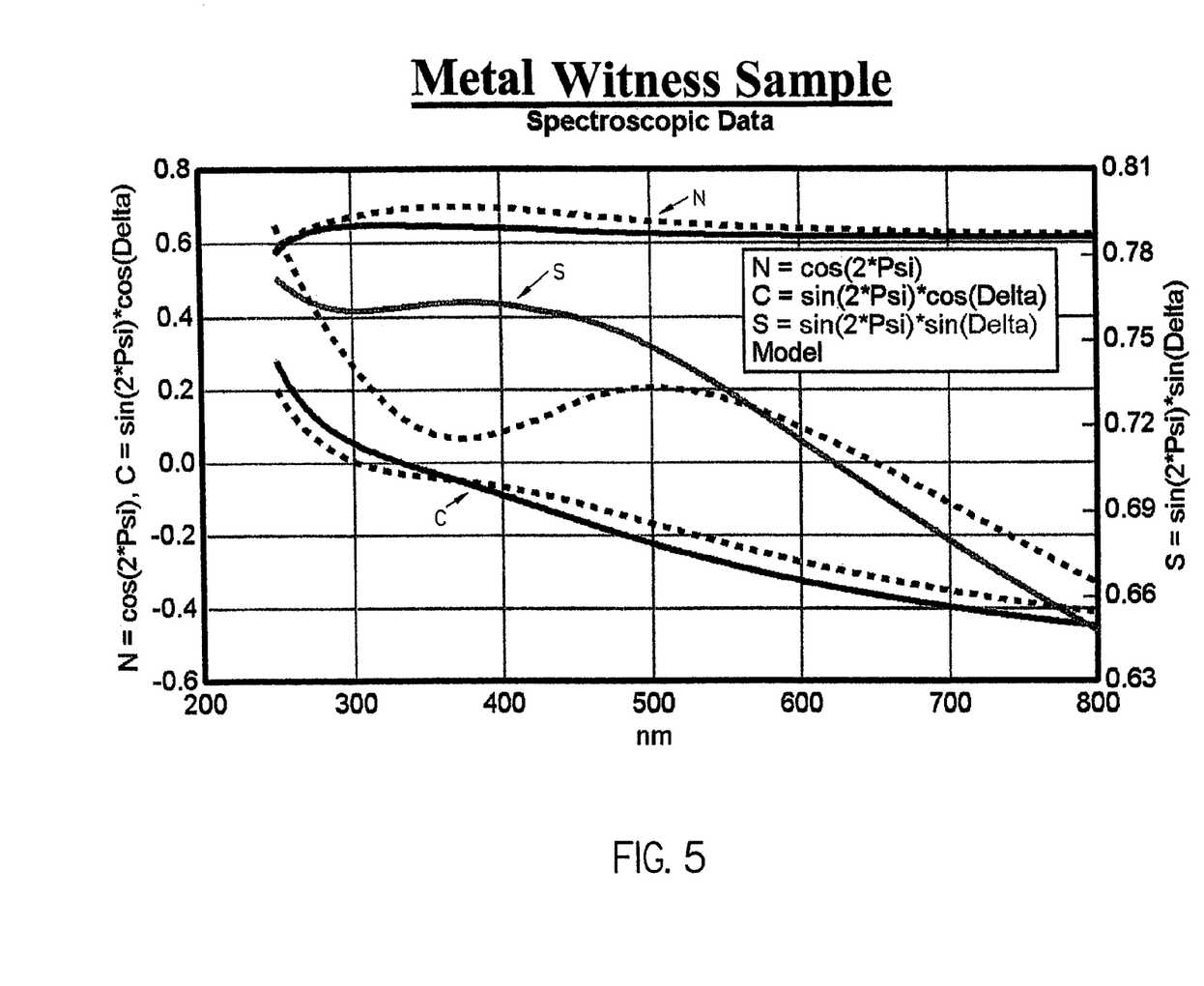
FIGS. 5-8, there are shown N, C and S spectra for the case of no film, (solid lines), and for the case where 10 Angstroms of Amorphous Silicon (a-Si), (dashed lines), are deposited on, respectively, a Tantalum Metal Substrate (FIG. 5); on a Silicon substrate with 20 Angstroms of Native Oxide (FIG. 6); on a Silicon Substrate with 250 Angstroms of Thermal Oxide (FIG. 7); and on a Silicon Substrate with 5000 Angstroms of Oxide present (FIG. 8).
Figure 6:
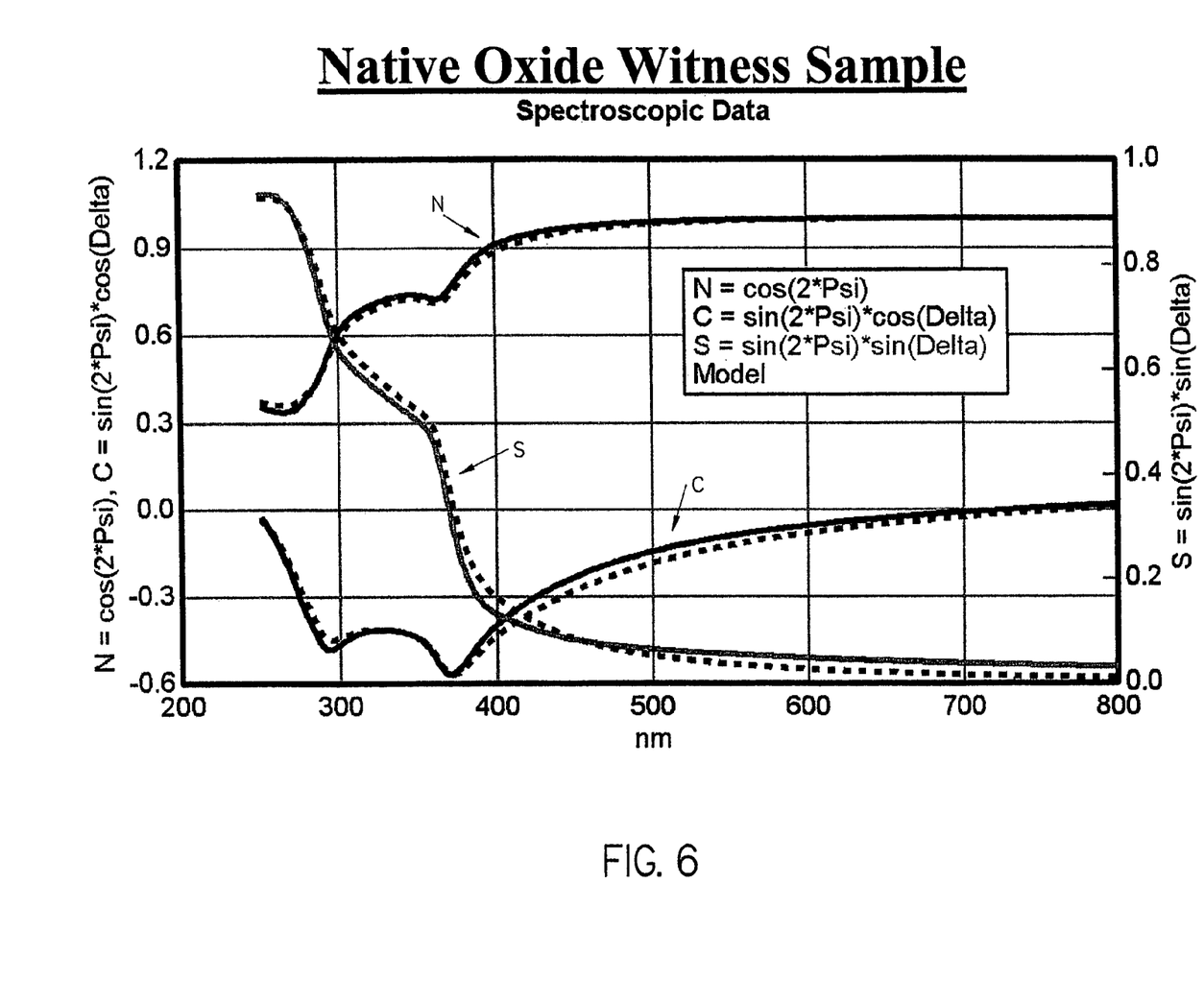
Figure 7:
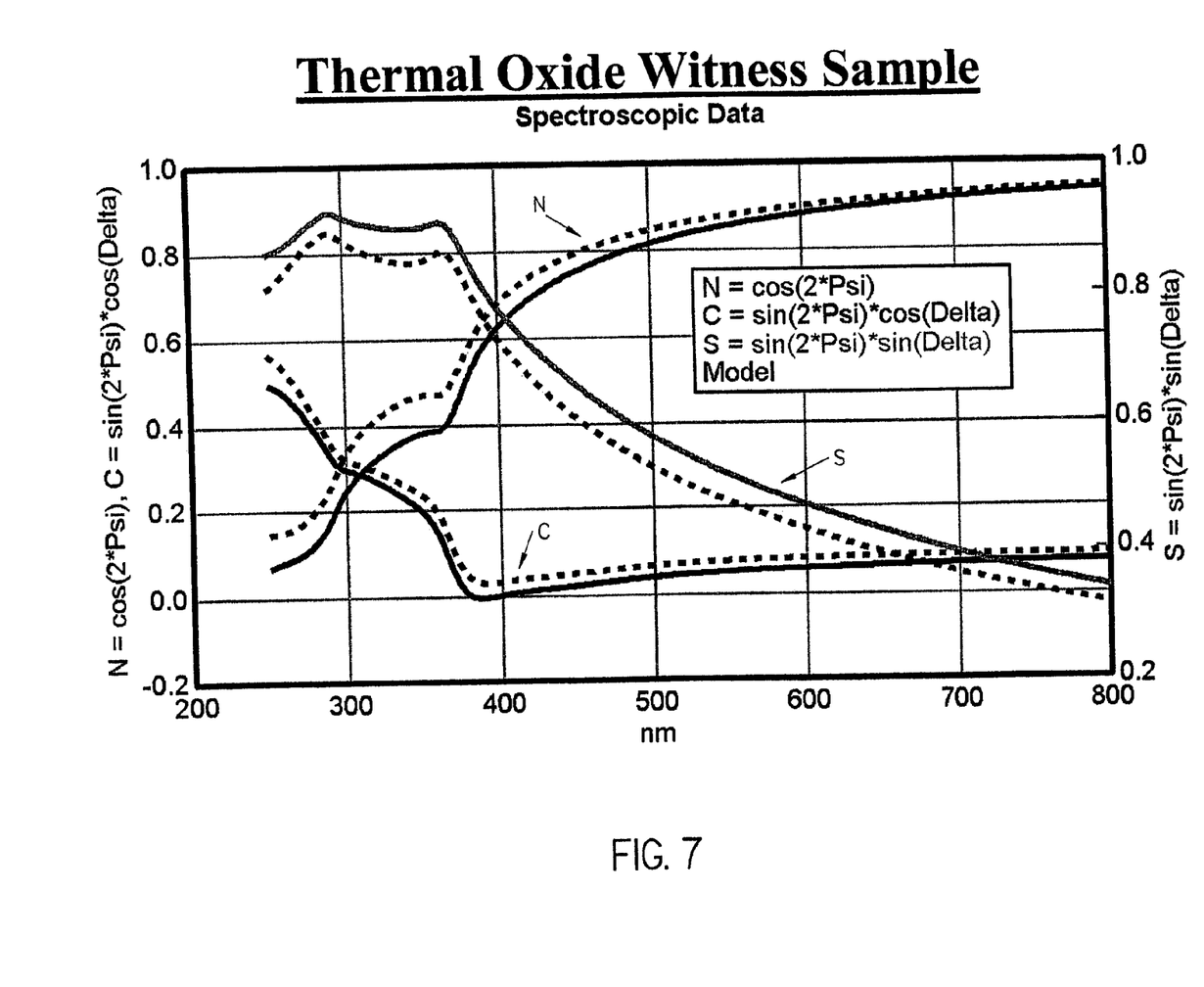

Turning now to the Drawings, FIGS. 1 and 2 demonstrate, on the same plot, typical ellipsometric PSI ($\psi$) and DELTA ($\Delta$) Spectra obtained for two samples. FIGS. 3 and 4 show differences in the PSI ($\psi$) and DELTA ($\Delta$) Spectra of FIGS. 1 and 2, respectively. The Difference Spectra of FIGS. 3 and 4 can at times obviate features in one spectra as compared to another "reference" spectra, which are not easily identified in the spectra per se. It is noted that a reference sample can be a bare substrate with perhaps only natural oxide present thereon, and spectra data obtained therefrom can be used to subtract baseline effects from sample data. Alternatively, both reference and sample can have, for instance, a similar sequence of high and low "K" layers present thereupon, and comparison of spectra obtained therefrom used to identify differences. Identified differences might be used to modify fabrication procedures, for instance, so that spectra obtained from references and sample become more identical. It is noted that the data in FIGS. 1-4 corresponds to Infra-red (IR) range wavelengths. While the disclosed invention can be practiced using any spectroscopic range of wavelengths from the Far Infra-red (FIR) through the Visible (VIS) and Deep Ultra-Violet (DUV) and (VUV). Infra-red (IR) spectra are often good candidates to which the disclosed invention can be beneficially applied. This is because IR range wavelengths probe, for instance, atomic bonds, and indication thereof in spectra can be difficult to identify. Difference spectra can serve to emphasize present, but subtle effects.

While FIGS. 1-4 demonstrate the possibility of using a Difference in Spectra obtained from two samples, or perhaps from one sample at different times during fabrication, it is often the case that a simple subtraction of PSI ($\psi$) and/or DELTA ($\Delta$) Spectra provides less than optimum results. In that light it is disclosed that it the disclosed invention method teaches that superior results can often be achieved by working with parameters derived from PSI ($\psi$) and DELTA ($\Delta$), which are known in the literature as N, C and S, said parameters being:

N=Cos(2$\psi$);
C=Sin(2$\psi$)Cos($\Delta$);
S=Sin(2$\psi$)Sin($\Delta$).

Use of N, C and S parameters provides advantages in that each is always bounded between −1 and +1, and ellipsometric data measurement sensitivity is often more uniform as compared to trigonometric PSI ($\psi$) and DELTA ($\Delta$). Further, as will be disclosed directly, spectroscopic data on thick transparent films exhibit more continuous behavior when plotted in terms of N, C and S.

To demonstrate the benefit of using N, C and S parameters in the method of the disclosed invention, an example involving obtaining data from a witness sample which is monitored during deposition of a thin film will be described. This scenario might be encountered, for instance, during Gate metal deposition in a MOSFET fabrication step. Before presenting said example, it is noted that a problem with monitoring deposition of very thin films onto MOSFET Gate Insulators using ellipsometry, is that ellipsometry is not always sensitive to the thickness of very thin films on transparent dielectric material which is less than about 100 Angstroms deep. Where a witness sample is monitored, however, it can comprise a transparent dielectric material layer which is much thicker, (eg. 5000 Angstroms). The methodology of the disclosed invention enables very sensitive monitoring of very thin layers of material deposited onto thick underlying transparent dielectric material.

Figure 8:
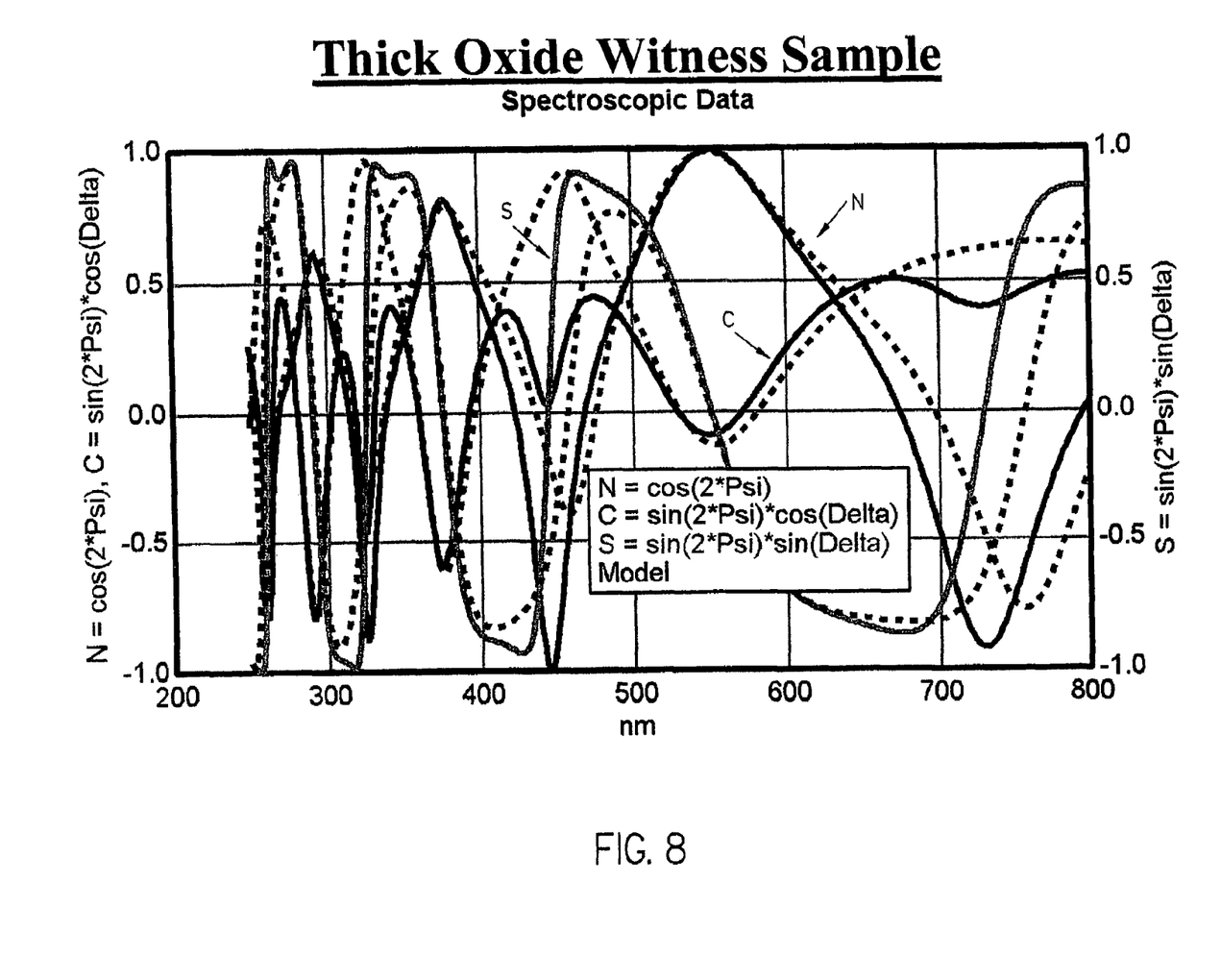

Turning now to FIGS. 5-8, there are shown N, C and S spectra for the case of no film, (solid lines), and for the case where 10 Angstroms of Amorphous Silicon (a-Si), (dashed lines), are deposited on, respectively, a Tantalum Metal Substrate (FIG. 5); on a Silicon Substrate with 20 Angstroms of Native Oxide (FIG. 6); on a Silicon Substrate with 250 Angstroms of Thermal Oxide (FIG. 7); and on a Silicon Substrate with 5000 Angstroms of Oxide present (FIG. 8). Note that while the dashed line are shifted from the solid lines in FIGS. 5-7, only FIG. 8 shows significant oscillations caused by deposition of 10 Angstroms of a-Si. That is, surprisingly, use of a Witness Sample which comprises thick Oxide at its Surface, greatly enhances the ability of ellipsometry to detect the presence of a 10 Angstrom film deposited thereonto.

Figure 9:
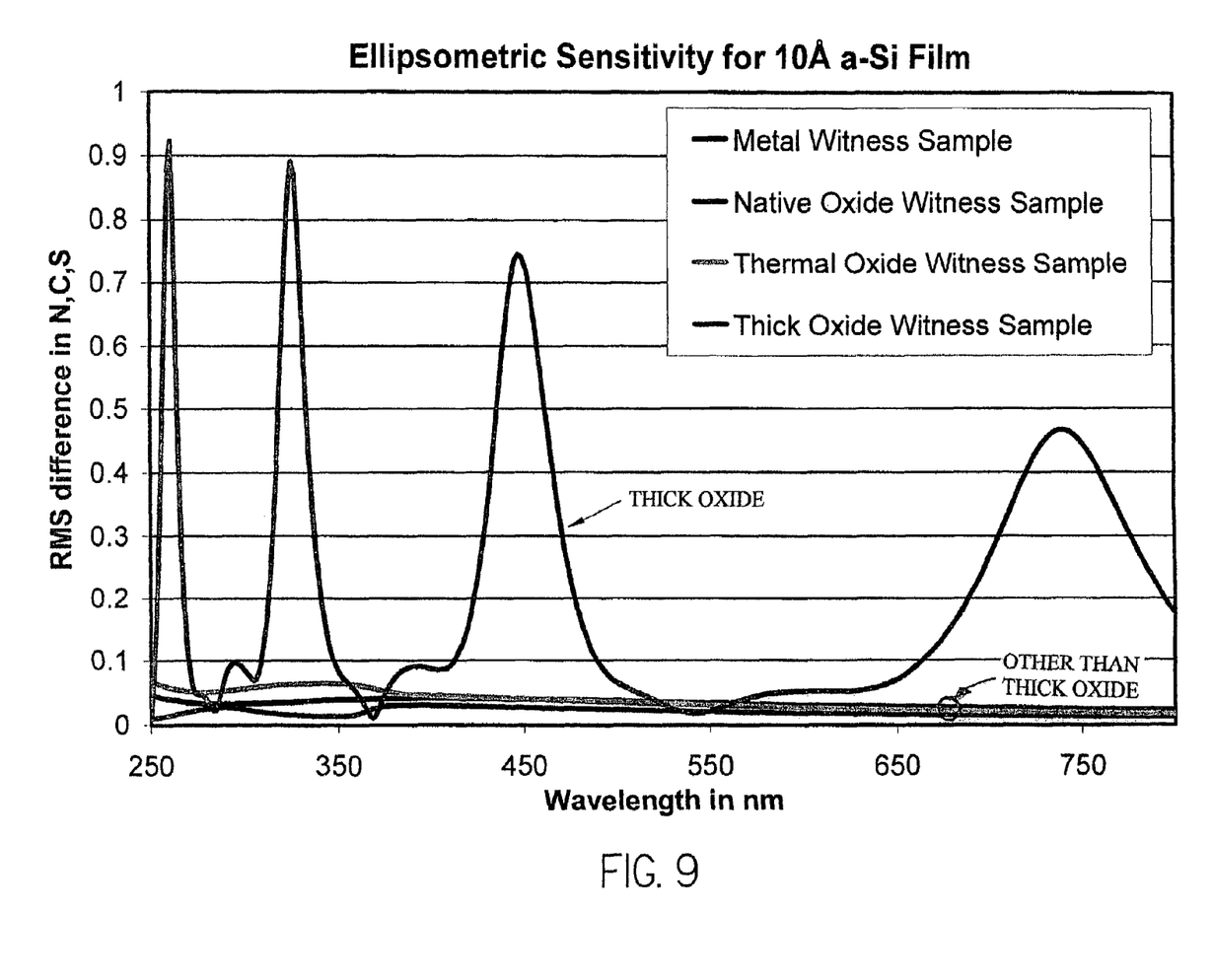
FIG. 9 plots the RMS values for the cases of FIGS. 5-8.
Figure 10:
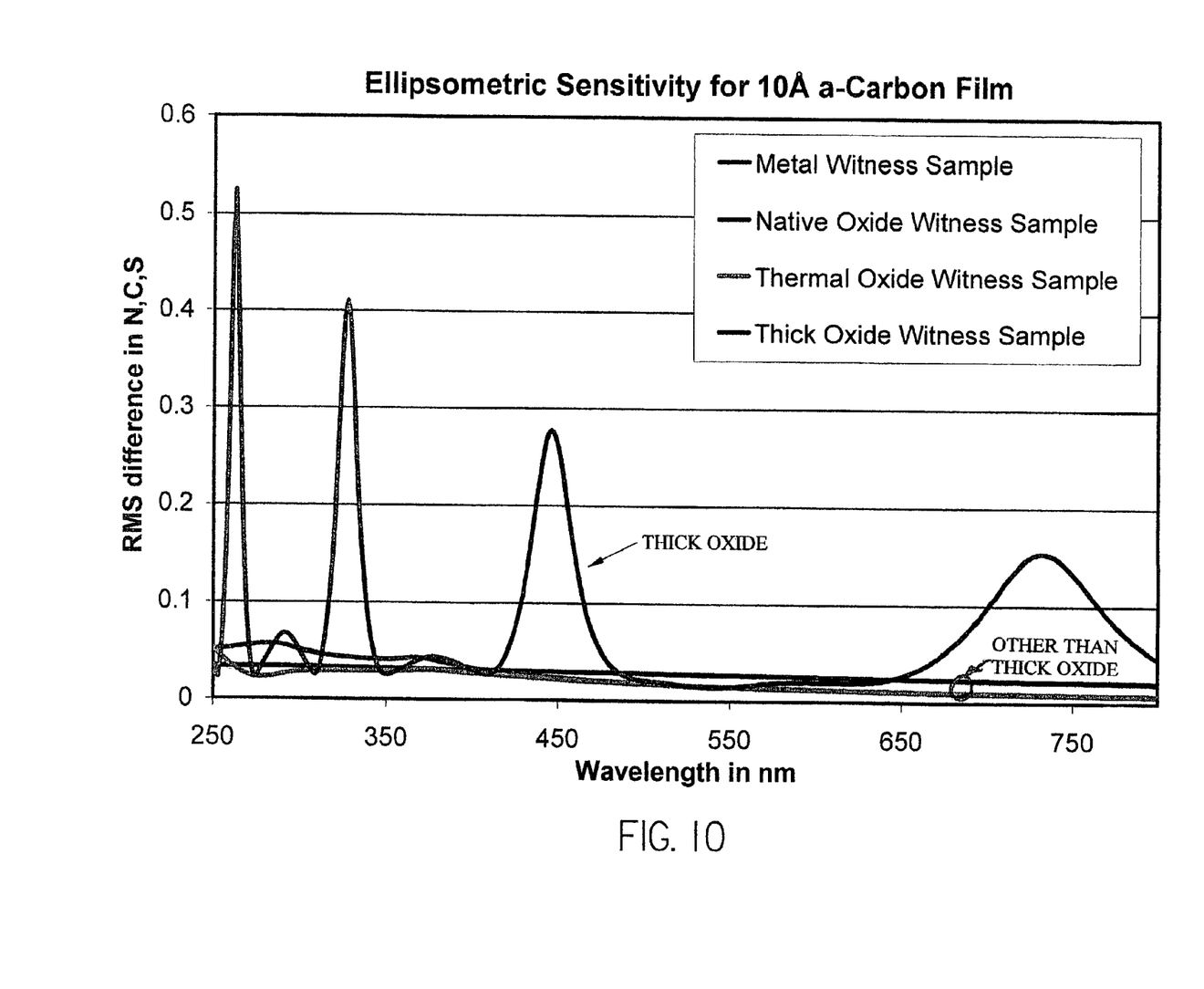
FIG. 10 shows results similar to those in FIG. 9, but for the case where 10 Angstroms of Amorphous Carbon (a-Carbon) are substituted for the Amorphous Silicon (a-Si).

It is acknowledged that FIG. 8 is difficult to interpret, and a preferred approach to displaying the data it contains is to calculate an RMS value which is calculated as:

$$\sqrt{\frac{(N_f - N_0)^2 + (C_f - C_0)^2 + (S_f - S_0)}{3}}$$

where "o" identifies data corresponding to when no thin film is present on the thick Oxide, and "f" identifies data corresponding to when thin film is present on the thick Oxide. (It is emphasised that "o" and "f" correspond to data obtained from a witness sample which comprises a thick dielectric). FIG. 9 plots the RMS values for the cases of FIGS. 5-8. Note that the data corresponding to FIG. 8 demonstrates an RMS sensitivity 20 times that of the data corresponding to FIGS. 5-7. FIG. 10 shows results similar to those in FIG. 9, but for the case where 10 Angstroms of Amorphous Carbon (a-Carbon) are substituted for the Amorphous Silicon (a-Si).

Figure 11:
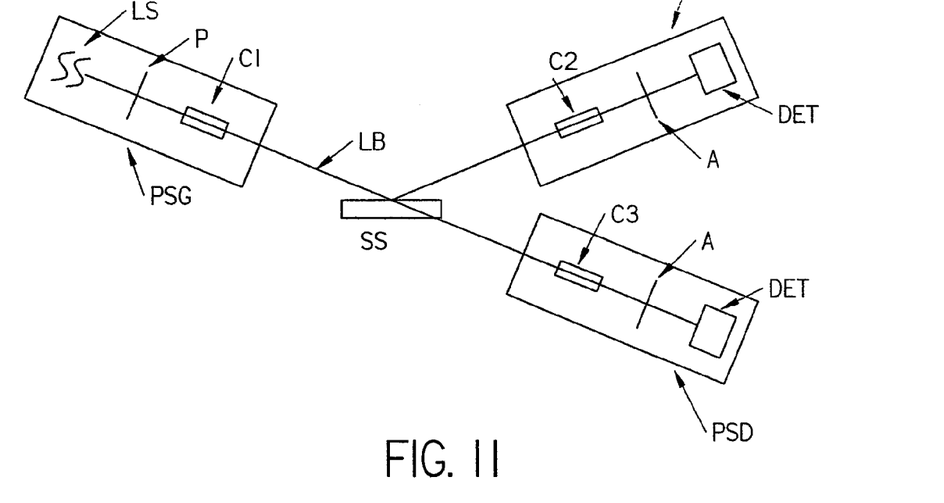
FIG. 11 is included to provide reference to an Ellipsometer System.

FIG. 11 is included to provide reference to an Ellipsometer System. Note that a Source of Electromagnetic Radiation (LS) provides a beam (LB) which has a polarization state set by Polarizer (P) and Optional Compensator (C1) prior to interaction with a Sample (SS). Shown after the Sample (SS) are both Reflection and Transmission scenarios, each of comprise an Analyzer (A) and Optional Compensator (C2) (C3). Note that indications of Polarization State Generator (PSG) and Polarization State Detector (PSD) are shown.

Figure 12:
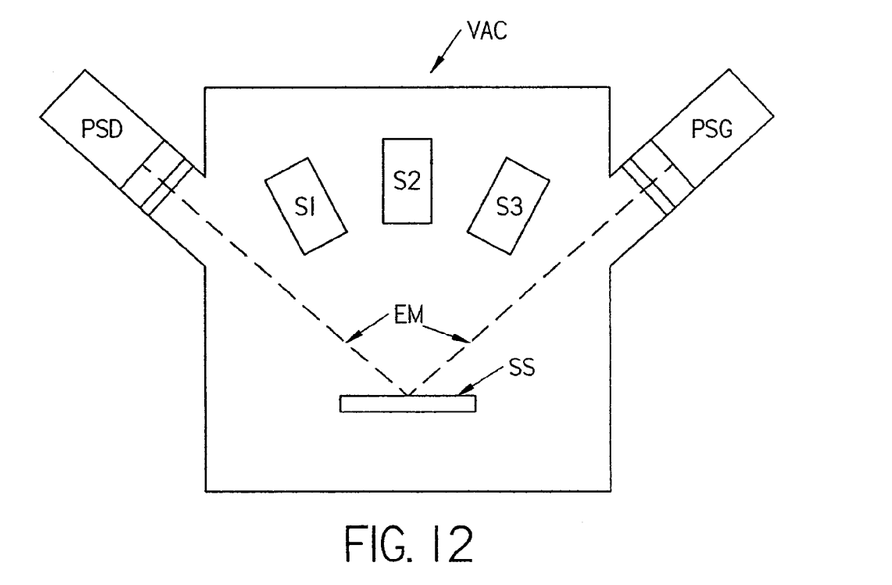
FIG. 12 demonstrates a system for depositing materials onto Samples (SS).

FIG. 12 demonstrates a system for depositing materials onto Samples (SS). Shown are a Vacuum Chamber (VAC) to which are affixed Polarization State Generator (PSG) and Polarization State Detector (PSD), as well as Sources (S1) (S2) (S3) of Materials to Deposit. Note that the Detector (DET) is to be considered to have means associated therewith that enable storing at least some data provided by said data detector in machine readable media; analyzing at least some of the data provided by said data detector and storing at least some of the results of said analysis in machine readable media; displaying at least some data provided by said data detector by electronic and/or non-electronic means; analyzing at least some of the data provided by said data detector and displaying at least some of the results of said analysis by electronic and/or non-electronic means; causing at least some data provided by said data detector to produce a signal which is applied to provide a concrete and tangible result; analyzing at least some of the data provided by said data detector and causing at least some thereof to produce a signal which is applied to provide a concrete and tangible result.

Figure 13:
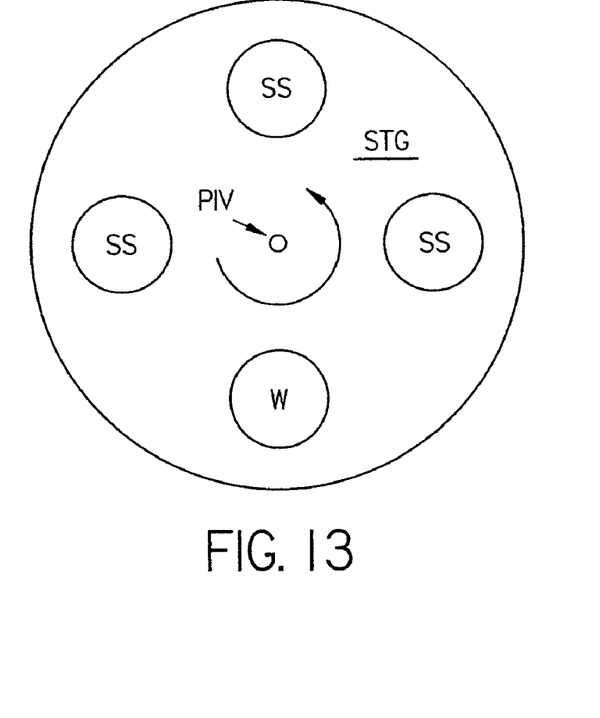
FIG. 13 demonstrates that a Sample (SS) can be on a rotatable stage (STG) which includes a Witness Sample (W).
Figure 14:
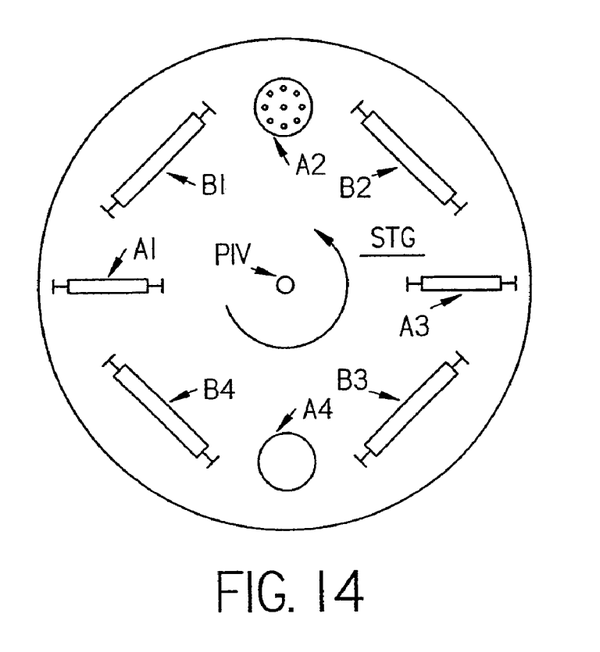
FIG. 14 demonstrates that the Samples (SS's) can be other than flat.

FIG. 13 demonstrates that a Sample (SS) can be on a rotatable stage (STG) which includes a Witness Sample (W). The Witness Sample (W) can have a Thick Dielectric present, atop which a thin film is deposited. FIG. 14 demonstrates that the Samples can be other than flat. For instance, cylindrical (A3), spherical (A4), with patterns (A2) (A1) thereupon can be present. The identifiers (B1) (B2) (B3) and (B4) can represent articles upon which a thin film is being deposited. Identifiers (A3) and (A4) can have a Thick Dielectric present thereupon.

Figure 15:
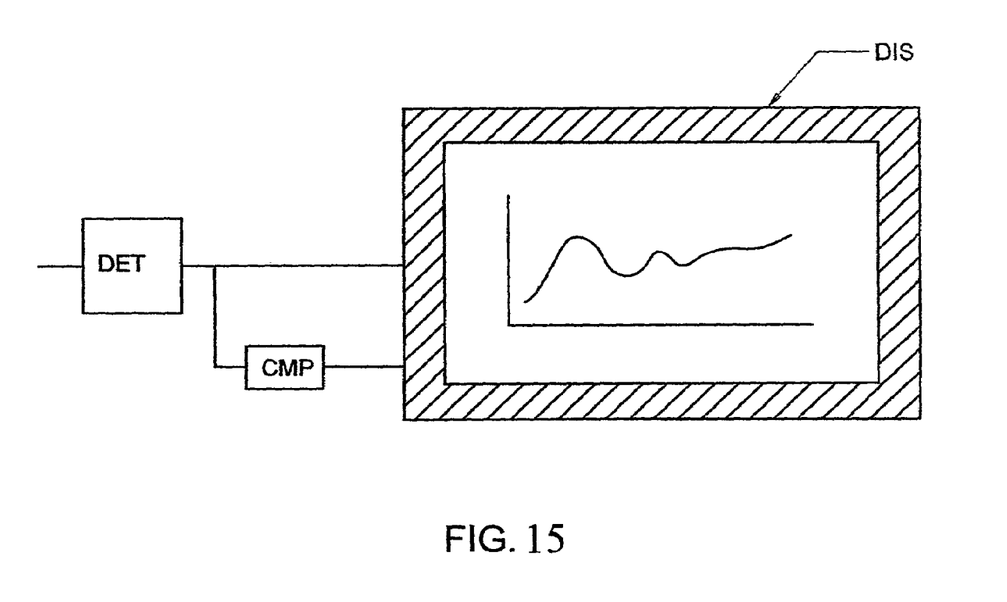
FIG. 15 demonstrates that data provided by a detector can be displayed or analyzed and displayed.

FIG. 15 demonstrates that data provided by a Detector (DET) can be displayed directly, or analyzed and displayed. It is to be noted that the Detector (DET) develops signals which are entered to the Display (DIS) or Computer (CMP), and that said signals can also be stored in machine readable media, such as magnetic media located in the Computer (CMP).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of monitoring fabrication of, or the end result of fabrication of a process sample comprised of a sequence of at least one very thin layer of material deposited thereonto, said layer having a thicknesses on the order of less than about 100 Angstroms, said method comprising the steps of:
   a) providing a process sample, and a witness sample other than a light fiber, said process sample having relatively no, or a very thin layer of a dielectric on a surface thereof, and said witness sample having a relatively thick dielectric on a surface thereof;
   b) before and/or during and/or after causing deposition of a thin layer of material on to both the prosess and witness samples, obtaining spectroscopic ellipsometric data from the witness sample by causing a polarized beam of polychromatic electromagnetic radiation to approach said witness sample at an oblique angle of incidence, interact with said witness sample and then enter a detector, to the end that said detector develops output data for said witness sample;
   c) analyzing said ellipsometric data to arrive at the thickness and/or optical constants of the material deposited onto the witness sample and attributing said result to the process sample;
   d) said method further comprising performing at least one selection from the group consisting of:
      storing at least some data provided by said data detector in machine readable media;
      analyzing at least some of the data provided by said data detector and storing at least some of the results of said analysis in machine readable media;
      displaying at least some data provided by said data detector by electronic and/or non-electronic means;
      analyzing at least some of the data provided by said data detector and displaying at least some of the results of said analysis by electronic and/or non-electronic means;
      causing at least some data provided by said data detector to produce a signal which is applied to provide a concrete and tangible result;
      analyzing at least some of the data provided by said data detector and causing at least some thereof to produce a signal which is applied to provide a concrete and tangible result.

2. A method as in claim 1 in which the spectroscopic data is derived from ellipsometric PSI ($\psi$) and/or DELTA ($\Delta$) vs. wavelength, and comprises at least one selection from the group consisting of:

$N = \cos(2\psi)$;
   $C = \sin(2\psi)\cos(\Delta)$;
   $S = \sin(2\psi)\sin(\Delta)$ where PSI ($\psi$) and DELTA ($\Delta$) are well known ellipsometric parameters related to a change in the ratio of orthogonal components of a polarized beam of electromagnetic radiation, and the phase angle therebetween, respectively, resulting from interaction with a sample, and N, C and S are calculated therefrom using the foregoing equations.

3. A method as in claim 2 in which the spectroscopic data comprises a difference in at least one selection from the group consisting of:

$(N_f - N_o)$;
   $(C_f - C_o)$; and
   $(S_f - S_o)$;

where $N_o$, $C_o$ and $S_o$ are values of N, C and S before deposition of a thin film onto said witness sample, and $N_f$, $C_f$ and $S_f$ are values of N, C and S after deposition of a thin film thereupon.

4. A method as in claim 2 in which the spectroscopic data comprises a difference in an RMS value calculated from:

$$\sqrt{\frac{(N_f - N_0)^2 + (C_f - C_0)^2 + (S_f - S_0)}{3}}$$

where:

$N_o = \cos(2\psi)$;
$C_o = \sin(2\psi)\cos(\Delta)$;
$S_o = \sin(2\psi)\sin(\Delta)$;

correspond to said witness sample before deposition of a thin film thereupon and:

$N_f = \cos(2\psi)$;
$C_f = \sin(2\psi)\cos(\Delta)$;
$S_f = \sin(2\psi)\sin(\Delta)$;

corresponds to said witness sample after deposition of said thin film thereupon;

wherein $N_o$, $C_o$ and $S_o$ are values of N, C and S before deposition of a thin film onto said witness sample, and $N_f$, $C_f$ and $S_f$ are values of N, C and S after deposition of a thin film thereupon.

5. A method as in claim 1 in which the witness sample onto which the thin film layer is deposited is comprised of at least one selection from the group consisting of:
- silicon dioxide on silicon $SiO_2$-SI;
- silicon dioxide $SiO_2$ on a witness sample;
- silicon oxy-nitride SiON on a witness sample;
- hafnium oxide HfO on a witness sample;
- hafnium oxide on silicon dioxide witness sample HfO—$SiO_2$.

6. A method as in claim 1 in which the electromagnetic radiation comprises wavelengths in at least one selection from the group consisting of:
- the far infrared FIR;
- the infrared IR;
- in the near infrared through the visible and into the near ultraviolet NIR-VIS-NUV;
- the ultraviolet UV;
- the deep ultraviolet DUV; and
- the vacuum ultraviolet VUV.

\* \* \* \* \*